United States Patent [19]
Ferzli

[11] Patent Number: 5,147,373
[45] Date of Patent: Sep. 15, 1992

[54] LAPAROSCOPIC INSTRUMENT

[76] Inventor: George S. Ferzli, 48 Merrick Ave., Staten Island, N.Y. 10301

[21] Appl. No.: 786,482

[22] Filed: Nov. 1, 1991

Related U.S. Application Data

[63] Continuation-in-part of Ser. No. 703,529, May 21, 1991, which is a continuation-in-part of Ser. No. 692,422, Apr. 29, 1991.

[51] Int. Cl.$^5$ .............................................. A61B 17/04
[52] U.S. Cl. .................................. 606/144; 606/206; 606/207; 606/148
[58] Field of Search .............. 606/142, 144, 148, 205, 606/206, 207

[56] References Cited

U.S. PATENT DOCUMENTS

| | | | |
|---|---|---|---|
| 2,518,994 | 8/1950 | Miller | 606/205 |
| 3,985,138 | 10/1976 | Jarvik | 606/144 X |
| 3,989,033 | 11/1976 | Halpern et al. | 606/206 X |
| 4,367,746 | 1/1983 | Derechinsky | 606/142 |
| 4,440,170 | 4/1984 | Golden et al. | 606/142 |

Primary Examiner—Randall L. Green
Assistant Examiner—Mary Beth O. Jones
Attorney, Agent, or Firm—Jordan and Hamburg

[57] ABSTRACT

A laparoscopic instrument includes an elongated member having two pairs of jaws with each pair being movable between open and closed positions. Finger grips are operably connected to each pair of jaws for actuating each pair of jaws between their open and closed positions. One of the two pairs of jaws is rotatably mounted.

15 Claims, 5 Drawing Sheets

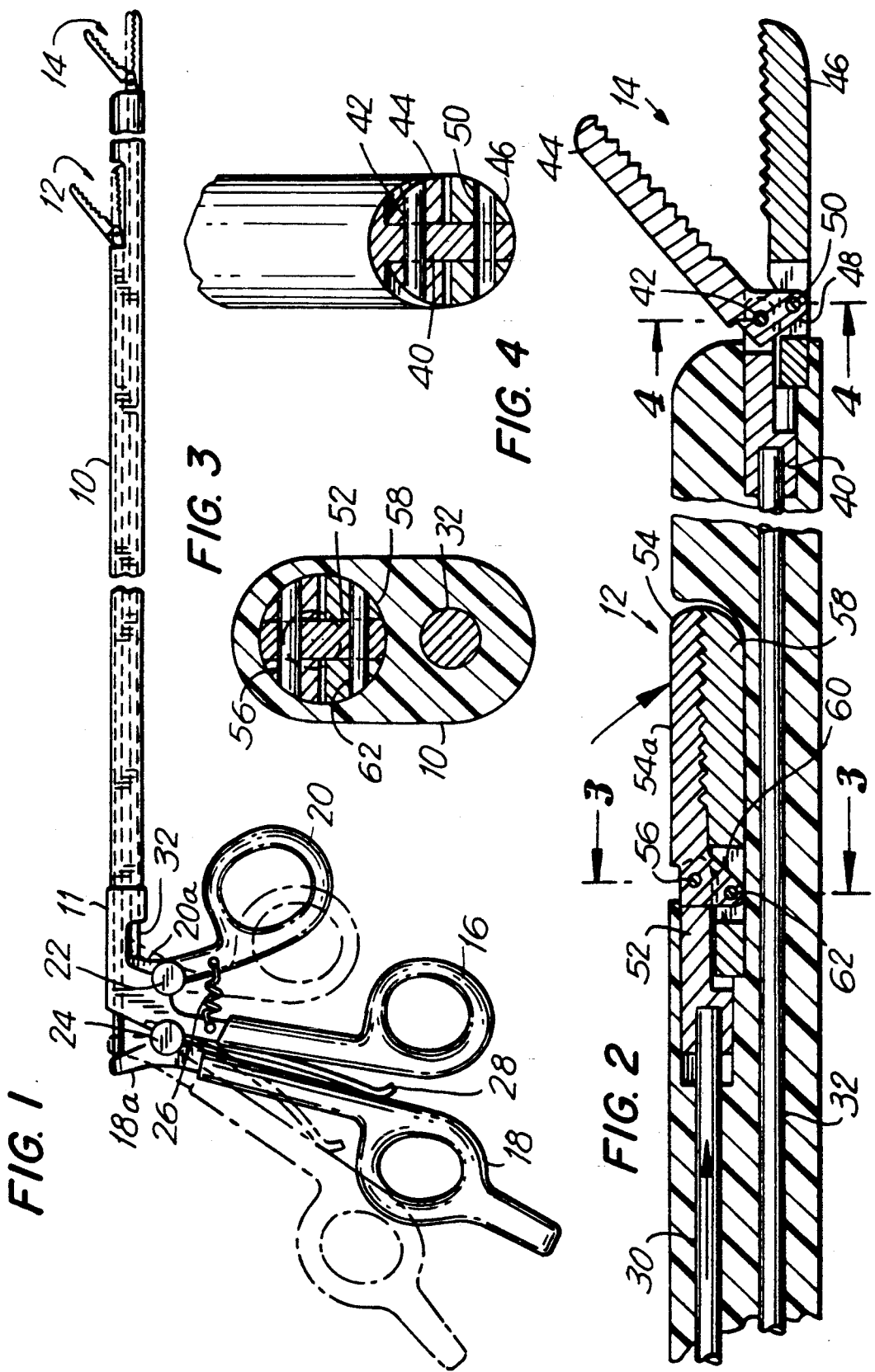

FIG. 9
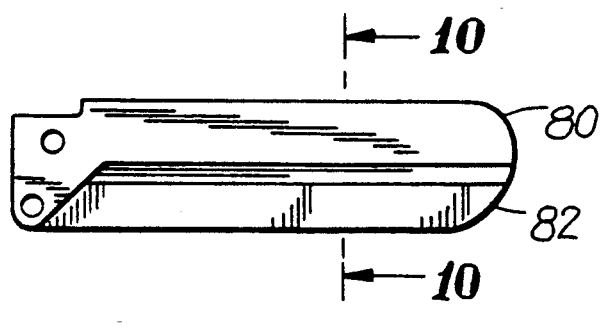
FIG. 10
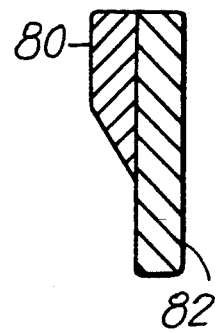
FIG. 11
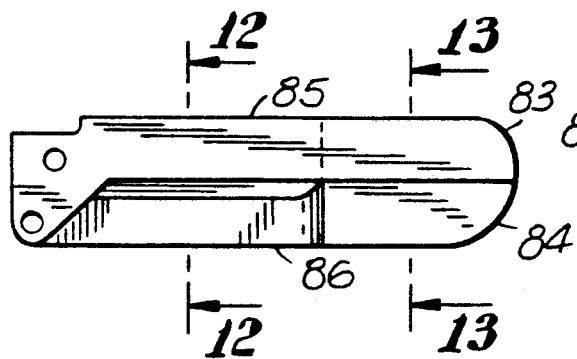
FIG. 12
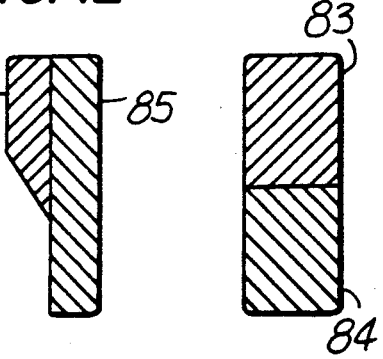
FIG. 13
FIG. 14
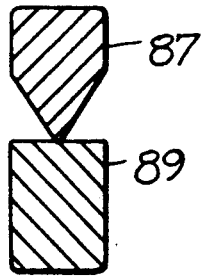
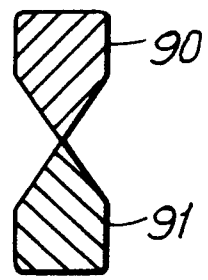
FIG. 15

LAPAROSCOPIC INSTRUMENT

This is a continuation-in-part application of U.S. Ser. No. 07/703,529, filed May 21, 1991, said Ser. No. 07/703,529 being a continuation-in-part application of U.S. Ser. No. 07/692,422, filed Apr. 29, 1991.

This invention relates to a laparoscopic instrument used during laparoscopic surgery.

In laparoscopic surgery, a miniature TV camera and surgical instruments are inserted through small punctures in the abdomen. The camera displays the patient's inner areas on a TV monitor which the surgeon watches while manipulating the instruments to perform the surgery. For example, laparoscopic cholecystectomy is used for removing the gallbladder. In order to remove the gallbladder, instead of making a six inch incision in the abdomen, a doctor using laparoscopy can cut a tiny incision in the abdomen and the patient's gallbladder can be pulled out through the incision. With laparoscopic surgery, there is minimal invasion such that there is a reduction in pain, fast recovery, and almost invisible scars.

The possibilities of laparoscopy is not limited to gallbladders but has also been used for ulcers, hernias, and appendectomies.

SUMMARY OF THE INVENTION

An object of the invention is to provide a laparoscopic instrument which can be inserted through a small opening in a person's body and which can be used during laparoscopic surgery for various purposes.

Another object of the invention is to provide a laparoscopic instrument having a pair of independently operated actuatable means such that a single instrument can perform more than one function during laparoscopic surgery.

A further object of the invention is to provide a laparoscopic instrument having a pair of independently operated actuatable means wherein one of said actuatable means is rotatable.

The above objects and other objects of the invention are achieved by providing a laparoscopic instrument which comprises an elongated member having two pairs of actuatable means with each pair being movable between open and closed positions and finger grip means operably connected to each pair of actuatable means for actuating each pair between their open and closed positions.

BRIEF DESCRIPTION OF THE DRAWINGS

FIG. 1 is an elevation view of a laparoscopic instrument according to one embodiment of the invention.

FIG. 2 is a partial longitudinal sectional view on a larger scale of the right-hand portion of the laparoscopic instrument shown in FIG. 1.

FIG. 3 is a cross-sectional view taken along the line 3—3 in FIG. 2.

FIG. 4 is a cross-sectional view taken along the line 4—4 in FIG. 2.

FIG. 9 is a partial elevational view of an alternate arrangement of one of the actuatable means which functions as a scissors.

FIG. 10 is a cross-sectional view taken along the line 10—10 in FIG. 9.

FIG. 11 is a partial elevational view showing a further alternate arrangement of one of the actuatable means.

FIG. 12 is a cross-sectional view taken along the line 12—12 in FIG. 11.

FIG. 13 is a cross-sectional view taken along the line 13—13 in FIG. 11.

FIG. 14 is a cross-sectional view of a further alternate arrangement wherein one of the actuatable means is arranged to perform a cutting action.

FIG. 15 is a view similar to FIG. 14 showing a further alternate arrangement.

DESCRIPTION OF THE PREFERRED EMBODIMENTS

Figure 5:
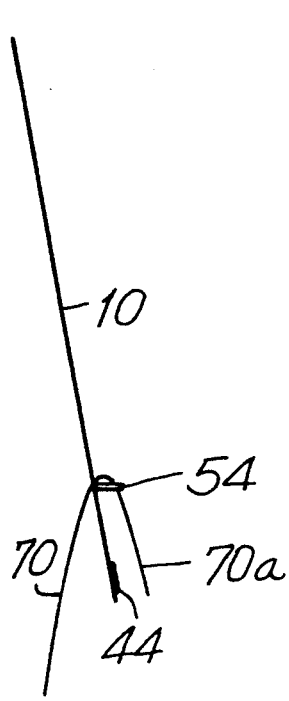
FIGS. 5 to 8 are schematic representations of one example of tying a knot in a suture using the laparoscopic instrument of the invention.

Referring to FIG. 1, the laparoscopic instrument shown therein includes an elongated barrel 10 having a pair of actuatable means, for example, alligator jaws 12 and 14, at the distal end thereof and finger grips at the proximal end thereof which are grasped and operated by the surgeon's fingers for opening and closing the alligator jaws 12 and 14. The alligator jaws 12 and 14 are operable to be closed, as shown in the middle of FIG. 2, or to be opened, as shown in FIG. 1, and the right-hand portion of FIG. 2. Accordingly, the surgeon can separately open and close the two alligator jaws 12, 14 in order to grasp and hold component parts used during an operation, for example, to grasp sutures and for tying knots in the sutures.

The instrument includes three finger grips 16, 18 and 20. The finger grip 16 is stationary in that it is fixed to a barrel end support 11 fixed to the proximal end of the barrel 10. The finger grip 20, on the other hand, is pivotably mounted on the barrel end support 11 at a pivot 22 while the finger grip 18 is pivotably mounted on the barrel end support 11 at a pivot 24. A spring 26 between the pivotal finger grip 20 and the fixed finger grip 16 pivotably biases the movable finger grip 20 in a clockwise position as shown in FIG. 1 to bias the alligator jaws 14 to a closed position. A spring 28 mounted on the pivot 24 extends downwardly to engage the movable finger grip 18 to bias the movable finger grip 18 in a clockwise direction as shown in FIG. 1 to thereby bias the alligator jaws 12 in a closed position. In FIG. 1, the two alligator jaws 12 and 14 are shown in an open position and correspond to the solid line position of the finger grips 18 and 20 in FIG. 1. The broken line representation of the finger grips 18 and 20 in FIG. 1 represent the closed position of the alligator jaws 12, 14.

The barrel 10 includes the two internal passageways which slidably support actuating rods 30 and 32. The end of the actuating rod 32 is connected to an extension 20a of the finger grip 20 such that pivoting of the finger grip 20 about its pivot 22 slides the operating rod 32 in the barrel 20.

The other end of the operating rod 32 is connected to a link 40 which is slidably mounted in the barrel 10 and which has an end pivotably connected to the upper jaw 44 at the pivot 42. The lower jaw 46 is connected to the barrel 10 and an extension 48 on the upper jaw 44 is pivotably connected to an inner portion of the lower jaw 46 at the pivot 50.

With the above arrangement, it will be seen from FIG. 2 that a the rod 32 is moved to the right from the position shown in FIG. 2, the upper jaw 44 will pivot clockwise about the pivot 50 to a closed position. Movement of the rod 32 to the left, as shown in FIG. 2, will pivot the upper jaw 44 from a closed position to its open position.

With the above arrangement, it will be seen that when the finger grip 20 is pivoted counterclockwise from the broken line to the solid line position shown in FIG. 1, the jaw 44 will move from its closed to its open position.

The end of the other actuating rod 30 is connected to an extension 18a of the finger grip 18 such that rotation of the finger grip 18 about its pivot 24 slides the operating rod 30 in the barrel 10.

The other end of the actuating rod 30 is connected to a link 52 which is slidably mounted within the barrel 10 and which has an end pivotably connected to the upper jaw 54 at the pivot 56. The lower jaw 58 is connected to the barrel 10 and an extension 60 on the upper jaw 54 is pivotably connected to an inner portion of the lower jaw 58 at the pivot 62.

With the above arrangement, it will be seen from FIG. 2 that as the rod 30 is moved to the left from the position shown in FIG. 2, the upper jaw 54 will pivot counterclockwise about the pivot 62 to an open position. Movement of the rod 30 to the right, as shown in FIG. 2, will pivot the upper jaw 54 from an open position to its closed position.

With the above arranqement, it will be seen that when the finger qrip 18 is pivoted olookwise from the broken line to the solid line position shown in FIG. 1, the jaw 54 will move from the closed to its open position.

With the above described arrangement, it will be seen that the surgeon is able to selectively operate the finger grips 18, 20 to independently open and close the two alligator jaws 12 and 14. In this way, the surgeon can use either alligator jaw 12 or 14 for grasping or releasing components used during the operation, for example, for grasping and releasing sutures for tying knots during a laparoscopic operation.

In addition to the above, the backside 54a of the alligator jaw 54 can be used to retain the suture during formation of a loop which is made while tying a knot. When tying a knot on a suture, it is necessary to form a loop in a length of the suture and then pass the free end of the suture through the loop to make the knot. Considering the fact that this is performed within the confines of the inside of a person's body and that the view is limited by what can be seen on a TV screen, further bearing in mind that the movements of the instruments are effected outside of the body by the grasping portion of the instrument, tying of a knot in a suture under such conditions can be a time consuming process. With the laparoscopic instrument of the present invention, the forming of a loop and a knot in a suture is greatly facilitated because as previously indicated, the loop can be passed over the backside 54a of the inner jaw 54 to support the loop as the instrument is manipulated and the other jaw 14 is used to grasp the free end of the suture and pass it through the loop to form the knot.

Figure 6:
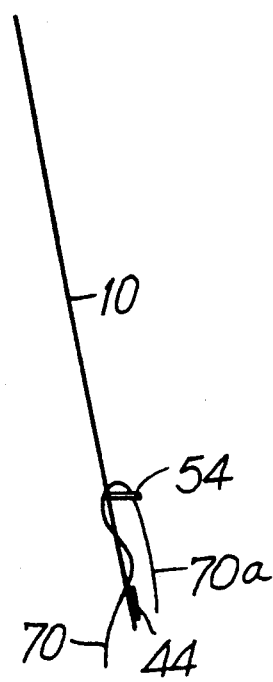
Figure 7:
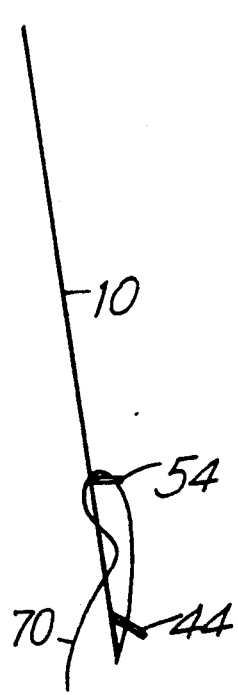
Figure 8:
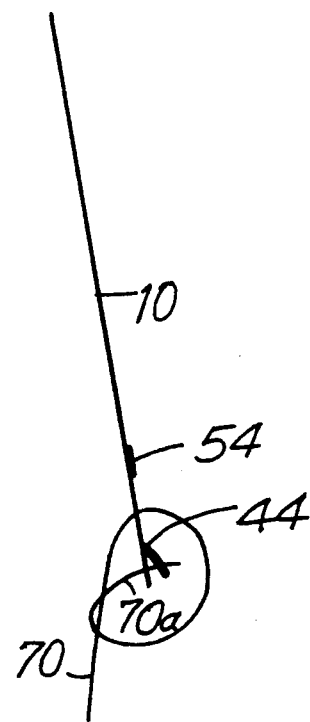

FIGS. 5 to 8 are schematic representations of one example of using the laparoscopic instrument for tying a knot in a suture. In FIG. 5 the intermediate jaw 54 is opened and the instrument manipulated to drape a suture 70 over the backside of the open intermediate jaw 54. Subsequently, the instrument is turned and manipulated to twist or wrap the suture 70 about the barrel 10 as shown in FIG. 6, and then the end jaws 44 grasps the free end 70a of the suture as shown in FIG. 7 whereupon the intermediate jaw 54 can be closed so that the grasped end 70a of the suture can be pulled through the loop 70b to make a knot as shown in FIG. 8.

Although the jaws in FIGS. 1 and 2 are shown as having serrations, the mating faces of the jaws may also have smooth surfaces. Although in the drawings the pivotal jaws 44, 54 are shown in the open position as disposed at an acute angle relative to the longitudinal axis of the barrel 10, either one or both pivotal jaws 44, 54 may be disposed perpendicular to the longitudinal axis of the barrel 10 when in their open position.

Although FIG. 3 shows an oval cross-sectional oonfiguration of the body 10, the overall configuration may be circular.

The length of the barrel of the laparoscopic instrument is generally longer than that shown in FIG. 1 as represented by the break in the longitudinal central part of FIG. 1. Also, the distances between the alligator jaws 12 and 14 may be variable as represented by the break as shown in the right-hand portion of FIG. 1.

As an alternate arrangement, an indentation may be provided in the backside 54a of the upper jaw 54 in order to facilitate retaining the loop of the suture during knot tying.

FIG. 9 shows an alternate arrangement wherein actuatable means in the form of scissor elements 80, 82 are provided to function as scissors. Thus the jaws 12 shown in FIGS. 1 and 2 may be replaced by the scissor elements 80, 82 shown in FIG. 9. Upon pivoting the movable scissor element 80 relative to the fixed scissor element 82, a scissor action is obtained for cutting sutures and other materials as may be desired during a laparoscopic operation. The scissor arrangement of FIGS. 9 and 10 may be used to replace either one or both of the jaws 12 and 14 shown in FIGS. 1 and 2.

FIG. 11 shows another arrangement wherein actuatable means have outer ends 83, 84 which function as a clamp and inner ends 85, 86 which function as scissors. Thus, the outer ends 83, 84 can be used to provide a grasping function, for example to grasp a suture, while the inner ends 85, 86 can be used to perform a cutting function.

FIG. 14 shows a further alternate arrangement wherein actuatable means 87 and 89 perform a cutting action in which the lower edge of the pivotal member 87 is formed as a cutting edge which abuts against the lower member 89 to perform a cutting action.

FIG. 15 is similar to FIG. 14 except that both member 90 and 91 have sharp edges such that the cutting action is performed somewhat like a cuticle scissors.

Figure 16:
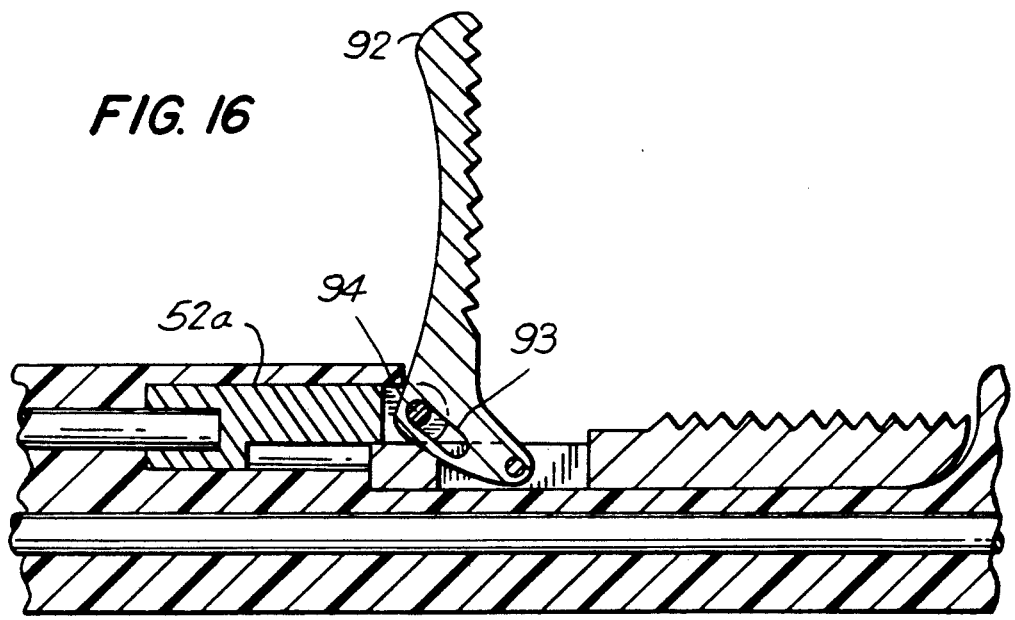
FIG. 16 is a partial cross-sectional view of an alternate arrangement for one of the actuatable means.

FIG. 16 shows another alternate arrangement wherein a pivotal jaw 92 is provided with a slot 93 which slidably receives a pin 94 connected to the slidable member 52a which is connected to the rod 30 shown in FIG. 2. In FIG. 16, the longitudinal extent of the jaw 92 extends perpendicularly to the longitudinal axis of the laparoscopic instrument. Also in FIG. 16, the upper side of the jaw 92 has an arcuate configuration to facilitate retaining the suture when it is draped thereover as shown in FIG. 5.

Figure 17:
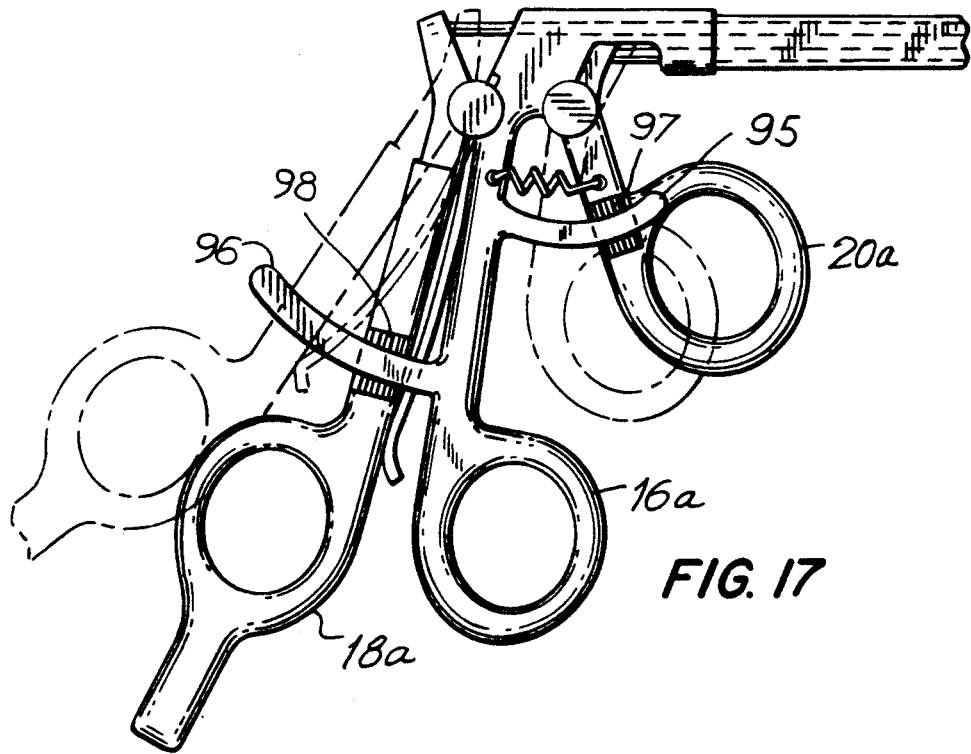
FIG. 17 shows another arrangement wherein clamping means are provided for the operation of the actuatable means.

FIG. 17 shows an alternate arrangement wherein clamping means are provided for clamping the jaws in various desired positions. Thus, arms 95 and 96 extend from the fixed finger grip 16a and the inner sides of these extending arms 95, 96 are provided with engageable teeth (e.g., ratchet teeth) which are engageable with engageable teeth (e.g., ratchet teeth) 97, 98 on the movable finger grips 20a and 18a, respectively. With this arrangement, the finger grips 20a, 18a can be locked or clamped in a desired position by the engagement between the teeth 97, 98 on the respective movable finger grips 20a, 18a and the matable teeth on the arms 95, 96. The surgeon can remove his finger from either of the movable finger grips 20a, 18a and such finger grip will be retained in the desired position by the engagement between the respective engageable teeth.

Figure 18:
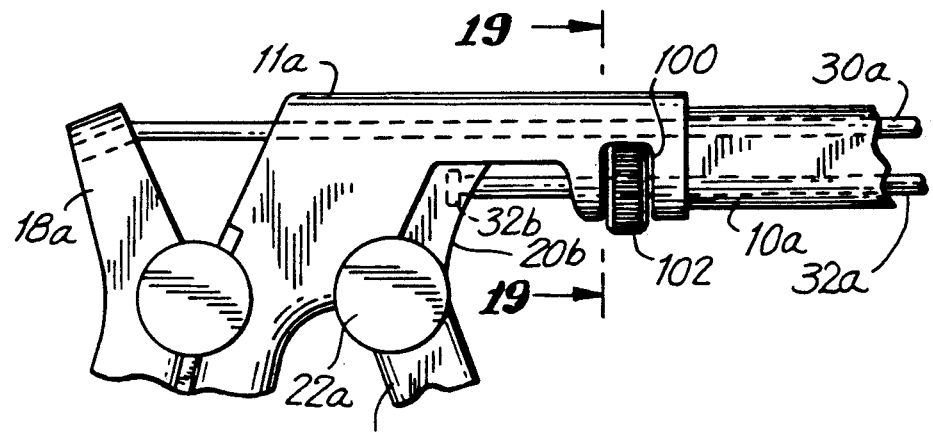
FIG. 18 is a partial view of the proximal end of a further embodiment wherein one of the jaw means is rotatable about a longitudinal axis.
Figure 19:
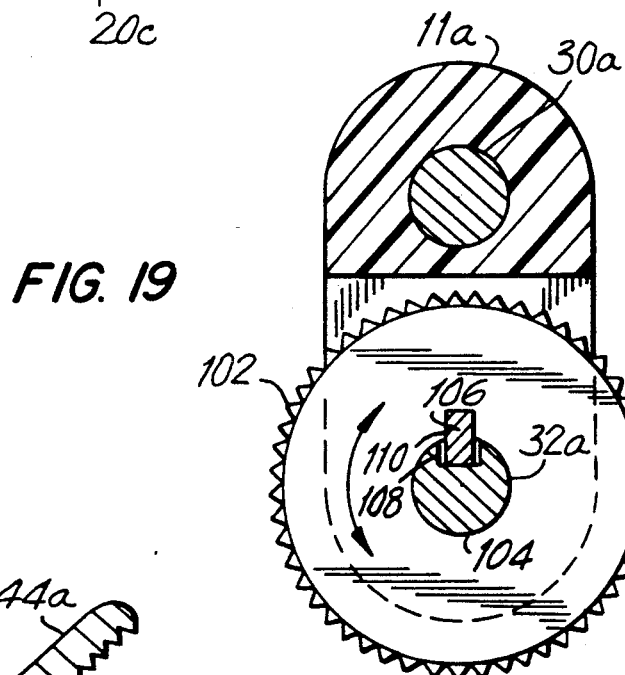
FIG. 19 is a cross-sectional view taken along the line 19—19 in FIG. 18.

FIG. 18 shows another alternate embodiment wherein the actuating rod 30a is slidably supported in the barrel 10a as in the FIG. 1 embodiment, but wherein the other actuating rod 32a is both slidably and rotatably mounted in the barrel 10a. As shown in FIG. 18, the barrel end support 11a has a groove 100 which receives a rotatable knob 102. The rotatable knob 102 extends outwardly of the sides of the barrel end support 11a as shown in FIG. 19 so that the rotatable knob 102 can be manually rotated by the surgeon.

The rotatable knob 102 has a central passage 104 which slidably but non-rotatably receives the actuating rod 32a. In this regard, a keyway 106 is provided in the knob 102 and a keyway 108 provided in the rod 32a for receiving a key 106 such that the key 106 prevents relative rotation between the knob 102 and the rod 32a while permitting the rod 32a to slide longitudinally in the passage 104.

Alternatively, instead of a keyway, a plurality of longitudinally extending serrations may be provided on a longitudinal portion of the rod 32a with such serrations being engageable with matable serrations on the inner cylindrical wall of the passage 104 in the knob 102. The matable serrations prevent relative rotation between the knob 102 and the rod 32a while allowing the rod 32a to slide longitudinally in the passage 104 of the know 102.

The outer cylindrical surface of the knob 102 may be provided with serrations or a knurl to facilitate manual turning of the knob 102.

The proximal end of the rod 32a has an end flange 32b received in a corresponding opening in the end portion 20b of the pivotably mounted finger grip 20c. Thus, the proximal end of the rod 32a with its flange 32b is rotatably received in the end portion 20b. However, relative longitudinal movement or sliding movement between the rod 32a and the end portion 20b is prohibited such that pivotal movement of the finger grip 20c effects sliding movement of the rod 32a.

It will be seen that the pivotal finger grip 20c is pivotal about the pivot 22a to effect sliding movement of the rod 32a as in the embodiment of FIG. 1. However, the rod 32a is also rotatably mounted in the end portion 20b of the finger grip 20c so that the rod 32a can be rotated by the knob 102.

The entire rod 32a is rotatably mounted in the elongated barrel 10a. The distal end of the rod 32a is connected to a link 40a which is also slidably and rotatably mounted in the distal end of the barrel 10a. The link 40a has an end pivotably connected to the jaw 44a at the pivot 42a. The jaw 46a has an inner extending part 48a which is rotatably mounted in the opening 10b in the distal end of the barrel 10a. The jaw 44a has a lateral projecting part which extends to a position juxtaposed to the inner extending portion 48a of the jaw 46a and a pivotal connection between the two jaws 44a, 46a is provided at 50a. It will be seen that the link 40a while being rotatably mounted in the barrel 10a is slidable in the barrel 10a such that slidable movement of the rod 32a effects opening and closing of the jaws 44a, 46a. The inner extension 48a of the jaw 46a, although rotatably mounted in the end opening 10b of the barrel 10a, is precluded from sliding longitudinally by a ring member 112 which extends into a circumferential groove 10c in the inner cylindrical wall of the end passage 10b and into a groove in the outer periphery of the inner extend part 48a of the jaw 46a.

The two jaws 44a, 46a are thus pivotably connected to one another at the pivot 50a, the jaw 44a being rotatable and longitudinally slidable and the jaw 50a being rotatable while being precluded from longitudinal sliding movement.

Although the jaw 46a is shown as non-pivotal, both jaws 46a and 44a may be pivotally mounted.

Figure 20:
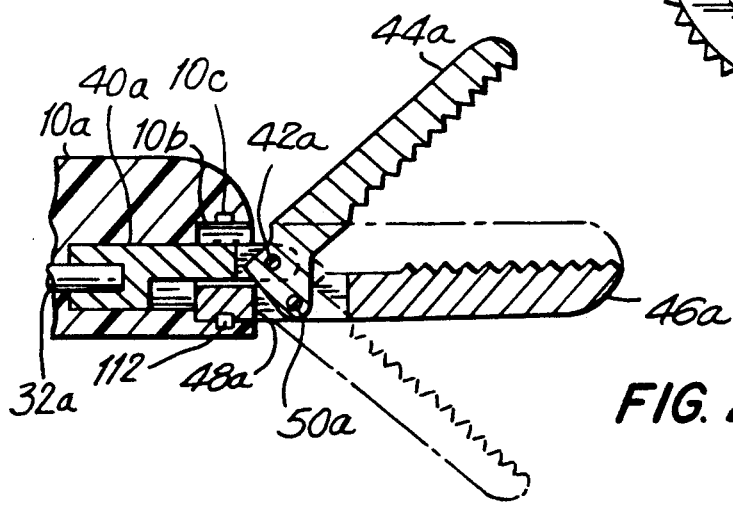
FIG. 20 is a partial view of the distal end of the laparoscopic instrument of FIG. 18.

With the above construction and arrangement, the surgeon can turn the knob 102 at the proximal end of the laparoscopic instrument and rotate jaws 44a, 46a to any desired rotatable position. FIG. 20, for example, shows in broken lines the position of the jaws 44a, 46a after having been rotated 180 degrees from the solid line position.

During laparoscopic surgery situations arise where it is desirable to effect relative rotation between the two sets of jaws in order to perform a particular procedure. The entire barrel 10a may be rotated by the surgeon, but when the entire barrel 10a is rotated both sets of jaws 12, 14 also rotate. With the above described arrangement, it is possible to obtain relative rotational movement between the two sets of jaws 12 and 14.

Although the present invention has been fully described by way of example with reference to the accompanying drawings, it is to be understood that various changes and modifications will be apparent to those skilled in the art. Therefore, unless such changes and modifications depart from the scope of the invention, they should be construed as being included therein.

What I claim is:

1. A laparoscopic instrument for use in laparoscopic surgery comprising an elongated member, said elongated member having a proximal end and a distal end, first jaw means comprising two relatively movable jaw elements disposed at said distal end, second jaw means comprising two relatively movable jaw members disposed intermediate said proximal and distal ends, said first and second jaw means being movable between open and closed positions, finger grip means on said proximal end of said elongated member, said finger grip means being operably connected to said first and second jaw means for actuating said first and second jaw means between said open and closed positions, and rotating means on said elongated member for rotating one of said jaw means relative to the other jaw means.

2. A laparoscopic instrument according to claim 1, wherein said first jaw means is designated an end jaw means and said second jaw means is designated an intermediate jaw means, said intermediate jaw means being longitudinally spaced from said end jaw means.

3. A laparoscopic instrument according to claim 2, wherein said finger grip maens comprises top finger grip elements selectively operable to independently actuate said intermediate and said end jaw means between their open and closed positions.

4. A laparoscopic instrument according to claim 2, wherein said elongated member has a recess, said intermediate jaw means being disposed in said recess when said intermediate jaw means is in its closed position.

5. A laparoscopic instrument according to claim 2, wherein one of said jaw elements of said end jaw means is mounted for pivotal movement relative to the other of said jaw elements.

6. A laparoscopic instrument according to claim 1, wherein one of said first and second jaw means comprises a rod means longitudinally slidable in said elongated member, said rotating means rotatably mounted said rod means in said elongated member.

7. A laparoscopic instrument according to claim 5, wherein said rod means has a knob means, and mounting means mounting said knob means on said rod means so as to preclude relative rotation between said knob means and said rod means, said rod means being longitudinally slidable relative to said knob means.

8. A laparoscopic instrument according to claim 2, wherein said end jaw means comprises pivot means pivotably mounting one of said jaw elements on the other jaw element such that said one jaw element is pivotable relative to the other jaw element.

9. A laparoscopic instrument according to claim 8, wherein said jaw means comprises an elongated rod, said pivot means being designated a first pivot means, and second pivot means pivotally connecting said rod to said one jaw element.

10. A laparoscopic instrument according to claim 9, wherein said rod, said first pivot means, said second pivot means, said one jaw element and said other jaw element are all rotatable together as a unit about a longitudinal axis which is coincident with the longitudinal axis of said elongated rod.

11. A laparoscopic instrument according to claim 5, wherein said elongated member comprises means for precluding longitudinal sliding movement of said other jaw element relative to said elongated member.

12. A laparoscopic instrument according to claim 5, wherein said rotating means comprises means for rotatably mounting said other jaw element about a rotational axis coincident with the longitudinal axis of said elongated rod.

13. A laparoscopic instrument according to claim 2, wherein said two jaw elements of said end jaw means each have a mating surface which mate when in said closed position, one of said jaw elements being a pivotal jaw element pivotably mounted on the other jaw element, said rotating means having means for rotatably supporting said end jaw means.

14. A laparoscopic instrument according to claim 2, wherein one of said jaw elements of said end jaw means is a pivotal jaw element pivotably mounted on said other jaw element between open and closed positions, said elongated member having a longitudinal axis, said pivotal jaw element having a jaw axis which is parallel to said longitudinal axis when said pivotal jaw element is in its closed position, said pivotal jaw element having its jaw axis disposed non-parallel to said longitudinal axis when said pivotal jaw element is in its open position.

15. A laparoscopic instrument according to claim 14, wherein said jaw axis of said pivotal jaw element extends at an acute angle relative to said longitudinal axis when said pivotal jaw element is in its open position.

* * * * *